US010383300B2

(12) United States Patent
Koerber

(10) Patent No.: US 10,383,300 B2
(45) Date of Patent: Aug. 20, 2019

(54) SPINACH VARIETY NUN 05048 SPS

(71) Applicant: NUNHEMS B.V., Nunhem (NL)

(72) Inventor: Frederike Koerber, Nunhem (NL)

(73) Assignee: NUNHEMS B.V., Nunhem (NL)

( * ) Notice: Subject to any disclaimer, the term of this patent is extended or adjusted under 35 U.S.C. 154(b) by 0 days.

(21) Appl. No.: 16/032,942

(22) Filed: Jul. 11, 2018

(65) Prior Publication Data

US 2018/0317416 A1   Nov. 8, 2018

Related U.S. Application Data

(60) Provisional application No. 62/582,999, filed on Nov. 8, 2017, provisional application No. 62/531,373, filed on Jul. 12, 2017.

(51) Int. Cl.
*A01H 5/12*  (2018.01)
*A01H 6/02*  (2018.01)

(52) U.S. Cl.
CPC ............... *A01H 5/12* (2013.01); *A01H 6/028* (2018.05)

(58) Field of Classification Search
None
See application file for complete search history.

(56) References Cited

U.S. PATENT DOCUMENTS

| 2013/0055454 A1* | 2/2013 | den Braber | A01H 5/12 800/260 |
| 2013/0055456 A1* | 2/2013 | den Braber | A01H 5/12 800/260 |
| 2014/0283195 A1* | 9/2014 | Jansen | C12N 15/8241 800/265 |
| 2015/0126380 A1 | 5/2015 | Van Dun | |
| 2015/0245570 A1 | 9/2015 | Vogelaar et al. | |

OTHER PUBLICATIONS

UPOV, *Spinacia oleracea* L. Guidelines (2016).*
Brotman et al., "Resistance gene homologues in melon are linked to genetic loci conferring disease and pest resistance", Theor Appl Genet, 2002, vol. 104, pp. 1055-1063.
Colijn-Hooymans, "Competence for regeneration of cucumber cotyledons is restricted to specific developmental stages", Plant Cell, Tissue and Organ Culture, 1994, vol. 39, pp. 211-221.
Needleman et al., "A General Method Applicable to the Search for Similarities in the Amino Acid Sequence of Two Proteins", Journal of Molecular Biology, 1970, vol. 48(3), pp. 443-453.
Parvathaneni et al., "Fingerprinting in Cucumber and Melon (*Cucumis* spp.) Genotypes Using Morphological and ISSR Markers", J. Crop Sci. Biotech., Mar. 2011, vol. 14, No. 1, pp. 39-43.
Ren et al., Shoot regeneration and ploidy variation in tissue culture of honeydew melon (*Cucumis melo* L. inodours), in Vitro Cell.Dev. Biol. Plant, 2013, No. 49, pp. 223-229.
Rice et al., "EMBOSS: The European Molecular Biology Open Software Suite", Trends in Genetics, 2000, vol. 16, Issue 6, pp. 276-277.
Vos et al., "AFLP: a new technique for DNA fingerprinting", Nucleic Acid Research, 1995, vol. 23, No. 21, pp. 4407-4414.
Wijnker et al., "Hybrid recreation by reverse breeding in *Arabidopsis thaliana*", Nature Protocols, 2014, vol. 9, pp. 761-772.
USDA, "Objective description of Variety Spinach (*Spinacia oleracea* L.)", Jun. 2015, ams.usda.gov/ under sites/default/files/media/83-Spinach%20ST-470-83%202015.pdf.
UPOV, Guidelines for the Conduct of Tests for Distinctness, Uniformity and Stability, TG/55/7 (Geneva 2007, last updated Mar. 16, 2016), upov.int/ under edocs/tgdocs/en/tg055.pdf.

* cited by examiner

*Primary Examiner* — Russell T Boggs
(74) *Attorney, Agent, or Firm* — Arent Fox LLP

(57) ABSTRACT

The disclosure provides a new and distinct hybrid variety of spinach, NUN 05048 SPS as well as seeds and plants and fruits thereof.

23 Claims, No Drawings

SPINACH VARIETY NUN 05048 SPS

CROSS-REFERENCE TO RELATED APPLICATIONS

The application claims the benefit of U.S. Patent Application Ser. No. 62/531,373, filed Jul. 12, 2017, and U.S. Patent Application Ser. No. 62/582,999, filed Nov. 8, 2017, which are incorporated herein by reference in their entirety.

FIELD OF THE INVENTION

The disclosure relates to the field of plant breeding and, more specifically, to spinach variety NUN 05048 SPS. The disclosure further relates to vegetative reproductions of NUN 05048 SPS, methods for tissue culture of NUN 05048 SPS and regenerating a plant from such a tissue culture, and to phenotypic variants of NUN 05048 SPS.

BACKGROUND

The goal of plant breeding is to combine various desirable traits in a single variety or hybrid. Such desirable traits may include greater yield, resistance to diseases, insects or other pests, tolerance to heat and drought, better agronomic quality, higher nutritional value, enhanced growth rate and improved fruit properties.

Breeding techniques take advantage of a plant's method of pollination. There are two general methods of pollination: a plant self-pollinates if pollen from one flower is transferred to the same or another flower of the same genotype. A plant cross-pollinates if pollen comes to it from a flower of a different genotype.

Plants that have been self-pollinated and selected for (uniform) type over many generations become homozygous at almost all gene loci and produce a uniform population of true breeding progeny of homozygous plants. A cross between two such homozygous plants of different lines produces a uniform population of hybrid plants that are heterozygous for many gene loci. The extent of heterozygosity in the hybrid is a function of the genetic distance between the parents. Conversely, a cross of two plants each heterozygous at a number of loci produces a segregating population of hybrid plants that differ genetically and are not uniform. The resulting non-uniformity makes performance unpredictable.

The development of uniform varieties requires the development of homozygous inbred plants, the crossing of these inbred plants to make hybrids, and the evaluation of the hybrids resulting from the crosses. Pedigree breeding and recurrent selection are examples of breeding methods that have been used to develop inbred plants from breeding populations. Those breeding methods combine the genetic backgrounds from two or more plants or various other broad-based sources into breeding pools from which new lines are developed by selfing and selection of desired phenotypes. The new plants are evaluated to determine which have commercial potential.

Spinach (*Spinacia oleracea*) is a flowering plant in the family Amaranthaceae. Spinach is an annual plant (rarely biennial) having flowers that mature into a small hard dry lumpy fruit cluster about 5-10 mm across containing several seeds.

Spinach has two stages in its life cycle including the vegetative, rosette stage in which the plant is marketable (about 35-40 days) and the bolting, seed stalk stage in which the plant is no longer marketable. Spinach can grow in a range of soils as long as they are moist and fertile, and particularly sandy loams that are high in organic matter.

While breeding efforts to date have provided a number of useful spinach lines with beneficial traits, there remains a great need in the art for new varieties with further improved traits. Such plants would benefit farmers and consumers alike by improving crop yields and/or quality. Some breeding objectives include varying the color, and texture of the leaf. Other objectives include disease or pest resistance, yield, suitability to various climatic circumstances, earliness, and fast growth.

SUMMARY OF VARIOUS EMBODIMENTS OF THE INVENTION

The disclosure provides for spinach variety NUN 05048 SPS, products thereof, and methods of using the same. NUN 05048 SPS is suitable for the baby leaf/fresh market.

In one aspect, the disclosure provides a seed of NUN 05048 SPS, wherein a representative sample of said seed has been deposited under Accession Number NCIMB 42856. The disclosure also provides for a plurality of seeds of NUN 05048 SPS. The spinach seed of NUN 05048 SPS may be provided as an essentially homogeneous population of spinach seed. The population of seed of NUN 05048 SPS may be particularly defined as essentially free from other seed. The seed population may be grown into plants to provide an essentially homogeneous population of spinach plants as described herein.

The disclosure also provides a plant grown from a seed of spinach variety NUN 05048 SPS and a plant part thereof. In another aspect, the disclosure provides for a hybrid spinach NUN 05048 SPS. The disclosure also provides for a progeny of NUN 05048 SPS. In another aspect, the disclosure provides a plant or a progeny retaining all or all but one, two or three of the "distinguishing characteristics" or all or all but one, two or three of the "morphological and physiological characteristics" of NUN 05048 SPS, and methods for producing that plant or progeny.

In one aspect, the disclosure provides a plant or a progeny having all the physiological and morphological characteristics of NUN 05048 SPS when grown under the same environmental conditions. In another aspect, the plant or progeny has all or all but one, two or three of the physiological and morphological characteristics of NUN 05048 SPS when measured under the same environmental conditions and evaluated at significance levels of 1%, 5% or 10% significance (which can also be expressed as a p-value), wherein a representative sample of seed of NUN 05048 SPS has been deposited under Accession Number NCIMB 42856. In another aspect, the plant or progeny has all or all but one, two or three of the physiological and morphological characteristics as listed in Table 1 for NUN 05048 SPS when measured under the same environmental conditions, and evaluated at significance levels of 1%, 5% or 10% significance (which can also be expressed as a p-value).

In another aspect, a plant of NUN 05048 SPS or a progeny thereof has 9, 10, or more or all of the following distinguishing characteristics: 1) Leaf blade blistering type; 2) Leaf blade lobing type; 3) Petiole length; 4) Petiole attitude type; 5) Leaf typical intensity of green color; 6) Leaf blade attitude type; and 7) Leaf blade shape (excluding basal lobes type).

In other aspects, the disclosure provides for a plant part obtained from NUN 05048 SPS, wherein said plant part is: a leaf, a harvested leaf, a part of a leaf, a fruit, a part of a fruit, pollen, an ovule, a cell, a petiole, a shoot or a part thereof, a stem or a part thereof, a root or a part thereof, a root tip, a cutting, a seed, a part of a seed, seed coat or another maternal tissue which is part of a seed grown on said variety, hypocotyl, cotyledon, a scion, a stock, a rootstock, a pistil, an anther, or a flower or a part thereof. Leaves are particularly important plant parts. In another aspect, the plant part obtained from NUN 05048 SPS is a cell, optionally a cell in a cell or tissue culture. That cell may be grown into a plant of NUN 05048 SPS.

The disclosure also provides a cell culture of NUN 05048 SPS and a plant regenerated from NUN 05048 SPS, which plant has all the characteristics of NUN 05048 SPS when grown under the same environmental conditions, as well as methods for regenerating NUN 05048 SPS. Alternatively, a regenerated plant may have one characteristic that is different from NUN 05048 SPS.

The disclosure further provides a vegetatively propagated plant of NUN 05048 SPS having all or all but one, two or three of the morphological and physiological characteristics of NUN 05048 SPS when grown under the same environmental conditions.

The disclosure also provides a spinach leaf produced on a plant grown from a seed of NUN 05048 SPS. In another aspect, the disclosure provides a seed growing or grown on a plant of NUN 05048 SPS (i.e., produced after pollination of the flower of NUN 05048 SPS).

Definitions

"Spinach" refers herein to plants of the species *Spinacia oleracea*, and leaves thereof. The most commonly eaten part of a spinach is the leaf.

"Cultivated spinach" refers to plants of *Spinacia oleracea* L (e.g., varieties, breeding lines or cultivars of the species *Spinacia oleracea* L), cultivated by humans and having good agronomic characteristics.

"Baby leaf spinach" are spinach leaves suitable for consumption, which are harvested earlier than standard spinach. They are more tender and suitable for use in, for example, salads.

The terms "NUN 05048 SPS", "spinach NUN 05048 SPS", "NUN 05048", "NUN 05048 F1", "05048 SPS" or "spinach 05048" are used interchangeably herein and refer to a NUN 05048 SPS plant, representative seed of which having been deposited under Accession Number NCIMB 42856.

A "seed of NUN 05048 SPS" refers to a spinach seed which can be grown into a plant of NUN 05048 SPS, wherein a representative sample of viable seed of NUN 05048 SPS has been deposited under Accession Number NCIMB 42856. A seed can be in any stage of maturity, for example, a mature, viable seed, or an immature, non-viable seed. A seed comprises an embryo and maternal tissues.

An "embryo of NUN 05048 SPS" refers to an "F1 hybrid embryo" as present in a seed of NUN 05048 SPS, a representative sample of said seed of NUN 05048 SPS having been deposited under Accession Number NCIMB 42856.

A "seed grown on NUN 05048 SPS" refers to a seed grown on a mature plant of NUN 05048 SPS or inside a fruit of NUN 05048 SPS. The "seed grown on NUN 05048 SPS" contains tissues and DNA of the maternal parent, NUN 05048 SPS. The "seed grown on NUN 05048 SPS" contains an F2 embryo. When said seed is planted, it grows into a first generation progeny plant of NUN 05048 SPS.

An "essentially homogeneous population of spinach seed" is a population of seeds where at least 97%, 98%, 99% or more of the total population of seed are seed of NUN 05048 SPS.

An "essentially homogeneous population of spinach plants" is a population of plants where at least 97%, 98%, 99% or more of the total population of plants are plants of NUN 05048 SPS.

The phrase "essentially free from other seed" refers to a population of seed where less than 3%, 2%, 1% or less of the total population of seed is seed that is not a spinach seed or, in another aspect, less than 3%, 2%, 1% or less of the total population of seed is seed that is not seed of NUN 05048 SPS.

"Tissue culture" or "cell culture" refers to a composition comprising isolated cells of the same or a different type or a collection of such cells organized into parts of a plant. Tissue culture of various tissues of spinach and regeneration of plants therefrom is well known and widely published (see, e.g., Ren et al., In Vitro Cell. Dev. Biol.—Plant (2013) 49:223-229; Colijn-Hooymans (1994), Plant Cell, Tissue and Organ Culture 39:211-217). Similarly, methods of preparing cell cultures are known in the art.

"UPOV descriptors" are the plant variety descriptors described for cucumber in the "Guidelines for the Conduct of Tests for Distinctness, Uniformity and Stability, TG104/5 (Geneva, last revised 2016), as published by UPOV (International Union for the Protection of New Varieties and Plants, available on the world wide web at upov.int) and which can be downloaded from the world wide web at upov.int/en/publications/tg-rom/tg055/tg_55_7.pdf (Geneva, 2007), and is herein incorporated by reference in its entirety.

"USDA descriptors" are the plant variety descriptors for cucumber as described in the document titled "OBJECTIVE DESCRIPTION OF VARIETY—Spinach *Spinacia oleracea* L.)" as published by the US Department of Agriculture, Agricultural Marketing Service, Plant Variety Protection Office, Beltsville, Md. 20705 and which can be downloaded from the World Wide Web at ams.usda.gov/ under sites/default/files/media/3-Spinach%20ST-470-83%202015.pdf, and is herein incorporated by reference in its entirety. "Non-USDA descriptors" are other descriptors suitable for describing spinach.

"RHS" or "RHS color chart" refers to the color chart of the Royal Horticultural Society of England, which publishes a botanical color chart quantitatively identifying colors by a defined numbering system. The chart may be purchased from Royal Horticulture Society Enterprise Ltd. RHS Garden; Wisley, Woking; Surrey GU236QB, UK, e.g., the RHS colour chart 2007.

"Plant part" includes any part of a plant, such as a plant organ, a plant cell, a plant protoplast, a plant cell tissue culture or a tissue culture from which a whole plant can be regenerated, a plant cell that is intact in a plant, a clone, a micropropagation, plant callus, a plant cell clump, a plant transplant, a vegetative propagation, a seedling, a leaf, a harvested leaf, a part of a leaf, a fruit, a part of a fruit, pollen, an ovule, an embryo, a petiole, a shoot or a part thereof, a stem or a part thereof, a root or a part thereof, a root tip, a cutting, a seed, a part of a seed, hypocotyl, cotyledon, a scion, a graft, a stock, a rootstock, a pistil, an anther, and a flower or parts of any of these and the like. Seed can be mature or immature. Pollen or ovules may be viable or non-viable. Also any developmental stage is included, such as seedlings, cuttings prior or after rooting, mature plants or leaves. Alternatively, a plant part may also include a plant seed which comprises maternal tissues of NUN 05048 SPS and an embryo having one or two sets of chromosomes derived from the parent plant (e.g., from NUN 05048 SPS). Such an embryo comprises two sets of chromosomes derived from NUN 05048 SPS if it is produced from self-pollination of NUN 05048 SPS, while an embryo derived from cross-fertilization of NUN 05048 SPS will comprise only one set of chromosomes from NUN 05048 SPS.

"Harvested plant material" refers herein to plant parts (e.g., leaves) detached from the whole plant), which have been collected for further storage and/or further use.

"Reference Variety" refers herein to Antalia, a commercial variety from company Nunhems, which has been planted in a trial together with NUN 05048 SPS. Characteristics of NUN 05048 SPS were compared to the characteristics of Antalia.

A plant having "all the physiological and morphological characteristics" of a referred-to-plant means a plant showing the physiological and morphological characteristics of the referred-to-plant when grown under the same environmental conditions, preferably in the same experiment; the referred-to-plant can be a plant from which it was derived, e.g., the progenitor plant, the parent, the recurrent parent, the plant used for tissue- or cell culture, etc. A physiological or morphological characteristic can be a numerical characteristic or a non-numerical characteristic. In one aspect, a plant has "all but one, two or three of the physiological and morphological characteristics" of a referred-to-plant, or "all the physiological and morphological characteristics" of Table 1 or "all or all but one, two or three of the physiological and morphological characteristics" of Table 1.

The physiological and/or morphological characteristics mentioned above are commonly evaluated at significance levels of 1%, 5% or 10% if they are numerical, or for having an identical degree (or type) if not numerical, if measured under the same environmental conditions. For example, a progeny plant or a Single Locus Converted plant or a mutated plant of NUN 05048 SPS may have one or more (or all) of the essential physiological and/or morphological characteristics of said variety listed in Table 1, as determined at the 5% significance level (i.e., $p<0.05$), when grown under the same environmental conditions.

"Distinguishing characteristics" or "distinguishing morphological and/or physiological characteristics" refers herein to the characteristics which distinguish the new variety from other spinach varieties, such as the Reference Variety (i.e., are different), when grown under the same environmental conditions. The distinguishing characteristics between NUN 05048 SPS and Reference Variety are described herein and also can be seen in Table 1. When comparing NUN 05048 SPS to other varieties, the distinguishing characteristics may be different. In one aspect, the distinguishing characteristics may include one, two, three or more (or all) of the characteristics listed in Table 1. All numerical distinguishing characteristics are statistically significantly different at $p<0.05$ between NUN 05048 SPS and the other variety (e.g., the Reference Variety).

NUN 05048 SPS has the following distinguishing characteristics when compared to the Reference Variety: 1) Leaf blade blistering type; 2) Leaf blade lobing type; 3) Petiole length; 4) Petiole attitude type; 5) Leaf typical intensity of green color; 6) Leaf blade attitude type; and 7) Leaf blade shape (excluding basal lobes type). This can be seen in Table 1, where the characteristics of NUN 05048 SPS are compared to characteristics of the Reference Variety, when grown under the same environmental conditions.

Thus, a spinach plant "comprising the distinguishing characteristics of NUN 05048 SPS" (such as a progeny plant) refers herein to a plant which does not differ significantly from said variety in the distinguishing characteristics above. Therefore, in one aspect, the disclosure provides a plant which does not differ significantly from NUN 05048 SPS in the distinguishing characteristics above.

Similarity and differences between two different plant lines or varieties can be determined by comparing the number of morphological and/or physiological characteristics that are the same (i.e., statistically not significantly different) or that are different (i.e., statistically significantly different) between the two plant lines or varieties using plants grown under the same environmental conditions. A numerical characteristic is considered to be "the same" when the value for a numeric characteristic is not significantly different at the 1% ($p<0.01$) or 5% ($p<0.05$) significance level, using one way analysis of variance (ANOVA), a standard method known to the skilled person. Non-numerical or "degree" or "type" characteristic are considered "the same" when the values have the same "degree" or "type" when scored using USDA and/or UPOV descriptors, if the plants are grown under the same environmental conditions.

A "plant line" is, for example, a breeding line which can be used to develop one or more varieties. A breeding line is typically highly homozygous.

"Hybrid variety" or "F1 hybrid" refers to the seeds harvested from crossing two inbred (nearly homozygous) parental lines. For example, the female parent is pollinated with pollen of the male parent to produce hybrid (F1) seeds on the female parent.

"Regeneration" refers to the development of a plant from cell culture or tissue culture or vegetative propagation.

"Vegetative propagation", "vegetative reproduction" or "clonal propagation" are used interchangeably herein and mean a method of taking a plant part and inducing or allowing that plant part to form at least roots, and also refer to the plant or plantlet obtained by that method. Optionally, the vegetative propagation is grown into a mature plant. The skilled person is aware of what plant parts are suitable for use in the method.

"Crossing" refers to the mating of two parent plants. The term encompasses "cross-pollination" and "selfing".

"Selfing" refers to self-pollination of a plant, i.e., the transfer of pollen from the anther to the stigma of the same plant.

"Cross-pollination" refers to the fertilization by the union of two gametes from different plants.

"Yield" means the total weight of all spinach leaves harvested per hectare of a particular line or variety. It is understood that "yield" is expressed as the weight of all spinach leaves harvested per hectare and can be obtained by multiplying the number of plants per hectare times the "yield per plant". "Marketable yield" means the total weight of all marketable spinach leaves, especially leaves which are not damaged or diseased, harvested per hectare of a particular line or variety. A "marketable leaf" is a leaf that has commercial value.

As used herein, the terms "resistance" and "tolerance" are used interchangeably to describe plants that show no symptoms or significantly reduced symptoms to a specified biotic pest, pathogen, abiotic influence or environmental condition compared to a susceptible plant. These terms are optionally also used to describe plants showing some symptoms but that are still able to produce marketable product with an acceptable yield.

The term "traditional breeding techniques" encompasses herein crossing, selfing, selection, doubled haploid production, embryo rescue, protoplast fusion, marker assisted selection, mutation breeding etc. as known to the breeder (i.e., methods other than genetic modification/transformation/transgenic methods), by which, for example, a genetically heritable trait can be transferred from one spinach line or variety to another. It optionally includes epigenetic modifications.

"Backcrossing" is a traditional breeding technique used to introduce a trait into a plant line or variety. The plant containing the trait is called the donor plant and the plant into which the trait is transferred is called the recurrent parent. An initial cross is made between the donor parent and the recurrent parent to produce a progeny plant. Progeny plants which have the trait are then crossed to the recurrent parent. After several generations of backcrossing and/or selfing the recurrent parent comprises the trait of the donor. The plant generated in this way may be referred to as a "single trait converted plant". The technique can also be used on a parental line of a hybrid.

"Progeny" as used herein refers to a plant obtained from a plant designated NUN 05048 SPS. A progeny may be obtained by regeneration of cell culture or tissue culture or parts of a plant of said variety or selfing of a plant of said variety or by producing seeds of a plant of said variety. In further aspects, progeny may also encompass plants obtained from crossing of at least one plant of said variety with another spinach plant of the same variety or another variety or line, or with wild spinach plants. A progeny may comprise a mutation or a transgene. A "first generation progeny" is the progeny directly derived from, obtained from, obtainable from or derivable from the parent plant by, e.g., traditional breeding methods (selfing and/or cross-pollinating) or regeneration (optionally combined with transformation or mutation). Thus, a plant of NUN 05048 SPS is the male parent, the female parent or both of a first generation progeny of NUN 05048 SPS. Progeny may have all the physiological and morphological characteristics of NUN 05048 SPS when grown under the same environmental conditions. Using methods such as backcrossing, recurrent selection, mutation or transformation, one or more specific characteristics may be introduced into said variety, to provide or a plant comprising all but 1, 2, or 3 of the morphological and physiological characteristics of NUN 05048 SPS.

The terms "gene converted" or "conversion plant" or "single locus converted plant" in this context refer to spinach plants which are developed by backcrossing wherein essentially all of the desired morphological and physiological characteristics of the parent variety or line are recovered, in addition to the one or more genes transferred into the parent via the backcrossing technique (optionally including reverse breeding or reverse synthesis of breeding lines) or via genetic engineering or through mutation breeding. Likewise, a "Single Locus Converted (Conversion) Plant" refers to plants developed by plant breeding techniques comprising or consisting of mutation and/or by genetic transformation and/or by backcrossing, wherein essentially all of the desired morphological and physiological characteristics of a spinach variety are recovered in addition to the characteristics of the single locus having been transferred into the variety via the backcrossing technique. In case of a hybrid, the gene may be introduced in the male or female parental line.

"Marker" refers to a readily detectable phenotype, preferably inherited in codominant fashion (both alleles at a locus in a diploid heterozygote are readily detectable), with no environmental variance component, i.e., a heritability of 1.

"Average" refers herein to the arithmetic mean.

The term "mean" refers to the arithmetic mean of several measurements. The skilled person understands that the appearance of a plant depends to some extent on the growing conditions of said plant. Thus, the skilled person will know suitable growing conditions for NUN 05048 SPS. The mean, if not indicated otherwise within this application, refers to the arithmetic mean of measurements on at least 10 different, randomly selected plants of a variety or line.

DETAILED DESCRIPTION OF VARIOUS EMBODIMENTS OF THE INVENTION

The disclosure relates to a plant of NUN 05048 SPS, wherein a representative sample of seeds of said variety was deposited under the Budapest Treaty, with Accession number NCIMB 42856. NUN 05048 SPS is suitable for the baby leaf/fresh market.

The disclosure also relates to a seed of a new spinach variety described herein, referred to as NUN 05048 SPS, wherein a representative sample of said seed was deposited under the Budapest Treaty, with Accession number NCIMB 42856.

In another aspect, the disclosure provides for a spinach plant part of NUN 05048 SPS, such as a leaf, a representative sample of seed from said variety has been deposited under the Budapest Treaty, with Accession number NCIMB 42856.

A seed of hybrid variety NUN 05048 SPS is obtainable by crossing the male parent of NUN 05048 SPS with the female parent of NUN 05048 SPS, and harvesting the seeds produced on the female parent. The resultant seeds of said variety can be grown to produce plants of said variety. In one aspect, a seed or a plurality of seeds of said variety are packaged into a container of any size or type (e.g., bags, cartons, cans, etc.). The seed may be disinfected, primed and/or treated with various compounds, such as seed coatings or crop protection compounds. The seed produces a plant of NUN 05048 SPS.

The disclosure also provides a plant of NUN 05048 SPS, or a leaf or other plant part thereof, produced from a seed, wherein a representative sample of said seeds has been deposited under the Budapest Treaty, with Accession Number NCIMB 42856.

The disclosure also provides a plant part obtained from NUN 05048 SPS, wherein said plant part is a leaf, a harvested leaf, a part of a leaf, a fruit, a part of a fruit, pollen, an ovule, a cell, a petiole, a shoot or a part thereof, a stem or a part thereof, a root or a part thereof, a root tip, a cutting, a seed, a part of a seed, seed coat or another maternal tissue which is part of a seed grown on said variety hypocotyl, cotyledon, a scion, a stock, a rootstock, a pistil, an anther, and a flower or a part thereof. Leaves are particularly important plant parts. In a further aspect, the plant part obtained from variety NUN 05048 SPS is a cell, optionally a cell in a cell or tissue culture. The cell may be grown into a plant of NUN 05048 SPS. A part of NUN 05048 SPS (or of a progeny of that variety or of a plant having all physiological and/or morphological characteristics but one, two or three of NUN 05048 SPS) further encompasses any cells, tissues, organs obtainable from the seedlings or plants in any stage of maturity.

The disclosure also provides for a food or feed product or a processed product comprising or consisting of a plant part described herein. The plant part may be a spinach leaf or part thereof and/or an extract from a leaf or another plant part described herein comprising at least one cell of NUN 05048 SPS. The food or feed product may be fresh or processed, e.g., dried, grinded, powdered, pickled, chopped, cooked, roasted, in a sauce, in a sandwich, pasted, puréed or concentrated, juiced, pickled, canned, steamed, boiled, fried, blanched and/or frozen, etc.

Such a plant part of NUN 05048 SPS can be stored and/or processed further. The disclosure thus also provides for a food or feed product comprising one or more of such parts, such as frozen, canned, chopped, cooked, roasted, in a sauce, in a sandwich, pasted, puréed or concentrated, juiced, dried, pickled, or powdered leaf from NUN 05048 SPS or from progeny of said variety, or from a derived variety, such as a plant having all but one, two or three physiological and/or morphological characteristics of NUN 05048 SPS.

In another aspect, the disclosure provides for a spinach leaf of NUN 05048 SPS, or a part of a leaf of said variety. The leaf can be in any stage of maturity, for example, immature (babyleaf) or mature. In another aspect, the disclosure provides for a container comprising a plurality of harvested spinach leaves or parts of leaves of said variety, or leaves of progeny thereof, or leaves of a derived variety. Marketable leaves are generally sorted by size and quality after harvest.

In another aspect, the plant, plant part or seed of NUN 05048 SPS is inside one or more containers, such as cans, boxes, crates, bags, cartons, Modified Atmosphere Packaging, films (e.g., biodegradable films), etc. comprising a plant or a plant part or a seed (fresh and/or processed) of NUN 05048 SPS. In a particular aspect, the container comprises a plurality of seeds of NUN 05048 SPS, or a plurality of plant parts of NUN 05048 SPS.

The disclosure further relates to a spinach variety NUN 05048 SPS, which—when compared to its REFERENCE VARIETY Antalia—has the following distinguishing characteristics: 1) Leaf blade blistering type; 2) Leaf blade lobing type; 3) Petiole length; 4) Petiole attitude type; 5) Leaf typical intensity of green color; 6) Leaf blade attitude type; and 7) Leaf blade shape (excluding basal lobes type), when the characteristics are determined at the 5% significance level for plants grown under the same environmental conditions. Also encompassed are parts of that plant.

In one aspect, a plant of NUN (5048 SPS or a progeny plant thereof, comprises all of the following morphological and/or physiological characteristics (i.e., average values of distinguishing characteristics, as indicated on the USDA Objective description of variety—spinach (unless indicated otherwise)): 1) Leaf blade blistering type; 2) Leaf blade lobing type; 3) Petiole length; 4) Petiole attitude type; 5) Leaf typical intensity of green color, 6) Leaf blade attitude type; and 7) Leaf blade shape (excluding basal lobes type), where the characteristics are determined at the 5% significance level for plants grown under the same environmental conditions. A part of this plant is also provided.

The disclosure further provides a spinach plant which does not differ from the physiological and morphological characteristics of the plant of NUN 05048 SPS as determined at the 1%, 2%, 3%, 4% or 5% significance level when grown under the same environmental conditions. In a particular aspect, the plants are measured in the same trial (e.g., the trial is conducted as recommended by the USDA or UPOV). The disclosure also comprises a part of said plant.

The disclosure also provides a tissue or cell culture comprising cells of NUN 05048 SPS. Such a tissue culture can, for example, be grown on plates or in liquid culture, or be frozen for long term storage. The cells of NUN 05048 SPS used to start the culture can be selected from any plant part suitable for vegetative reproduction, or in a particular aspect, can be cells of an embryo, meristem, a cotyledon, a hypocotyl, pollen, a leaf, an anther, a root, a root tip, a pistil, a petiole, a flower, a fruit, seed or a stem. In another particular aspect, the tissue culture does not contain somaclonal variation or has reduced somaclonal variation. The skilled person is familiar with methods to reduce or prevent somaclonal variation, including regular re-initiation.

In one aspect, the disclosure provides a spinach plant regenerated from the tissue or cell culture of NUN 05048 SPS, wherein the regenerated plant is not significantly different from NUN 05048 SPS in all, or all but one, two or three, of the physiological and morphological characteristics (determined at the 5% significance level when grown under the same environmental conditions). Optionally, the plant has one, two or three the physiological and morphological characteristics that are affected by a mutation or by transformation. In another aspect, the disclosure provides a spinach plant regenerated from the tissue or cell culture of NUN 05048 SPS, wherein the plant has all of the physiological and morphological characteristics of said variety determined at the 5% significance level when grown under the same environmental conditions. Similarity or difference of a characteristic is determined by measuring that characteristics on a representative number of plants grown under the same environmental conditions, determining whether type/degree characteristics are the same and determining whether numerical characteristics are different at the 5% significance level.

NUN 05048 SPS, or its progeny, or a plant having all physiological and/or morphological characteristics but one, two or three which are different from those of NUN 05048 SPS, can also be reproduced using vegetative reproduction methods. Therefore, the disclosure provides for a method of producing a plant, or a plant part, of NUN 05048 SPS, comprising vegetative propagation of said variety. Vegetative propagation comprises regenerating a whole plant from a plant part of NUN 05048 SPS or from a progeny or from or a plant having all physiological and/or morphological characteristics of said variety but one, two or three different characteristics, such as a cutting, a cell culture or a tissue culture.

The disclosure also provides methods of vegetatively propagating a part of the plant of the disclosure NUN 05048 SPS. In certain aspects, the method comprises: (a) cultivating tissue or cells capable of being propagated from NUN 05048 SPS to obtain proliferated shoots; and (b) rooting said proliferated shoots, to obtain rooted plantlets. Steps (a) and (b) may also be reversed, i.e., first cultivating said tissue to obtain roots and then cultivating the tissue to obtain shoots, thereby obtaining rooted plantlets. The rooted plantlets may then be further grown, to obtain plants. In one aspect, the method further comprises step (c) growing plants from said rooted plantlets. Therefore, the method also comprises regenerating a whole plant from a part of NUN 05048 SPS. In a particular aspect, the part of the plant to be propagated is a cutting, a cell culture or a tissue culture.

The disclosure also provides for a vegetatively propagated plant of NUN 05048 SPS (or from progeny of NUN 05048 SPS or from or a plant having all but one, two or three physiological and/or morphological characteristics of NUN 05048 SPS), wherein the plant has all of the morphological and physiological characteristics of NUN 05048 SPS when the characteristics are determined at the 5% significance level for plants grown under the same conditions. In an aspect, the propagated plant has all but one, two or three of the morphological and physiological characteristics of NUN 05048 SPS when the characteristics are determined at the 5% significance level for plants grown under the same conditions. A part of said propagated plant or said propagated plant with one, two or three differences is also included.

In another aspect, the disclosure provides a method for producing a spinach plant part, such as a leaf, comprising growing a plant of NUN 05048 SPS until it develops at least one leaf, and collecting the leaf. In a particular aspect, the leaf is collected at harvest maturity. In another aspect, the leaf is collected at babyleaf stage. In another particular aspect, all leaves in a field can be harvested at the same time. A plant of NUN 05048 SPS can be produced by seeding directly in the soil (e.g., the field) or by germinating the seeds in a controlled environment (e.g., a greenhouse) and optionally then transplanting the seedlings into the field. Spinach can also be grown entirely in greenhouses. For example, a seed is sown into a prepared seed bed in a field where the plant remains for its entire life.

In still another aspect, the disclosure provides a method of producing a spinach plant, comprising crossing a plant of NUN 05048 SPS with a second spinach plant at least once, allowing seed to develop and optionally harvesting said progeny seed. The skilled person can select progeny from said crossing. Optionally, the progeny (grown from the progeny seed) is crossed twice, thrice, or four, five, six or seven times, and allowed to set seed. In one aspect, the first "crossing" further comprises planting seeds of a first and a second parent spinach plant, often in proximity so that pollination will occur; for example, mediated by insect vectors. The second spinach plant may, for example, be a line or variety of the species Spinacia oleracea, or other Spinacia species. Alternatively, pollen can be transferred manually. Where the plant is self-pollinated, pollination may occur without the need for direct human intervention other than plant cultivation. After pollination the plant can produce seed.

The disclosure also provides a method for developing a spinach plant in a spinach breeding program, using NUN 05048 SPS, or its parts as a source of plant breeding material. Suitable plant breeding techniques are recurrent selection, backcrossing, pedigree breeding, mass selection, mutation breeding and/or genetic marker enhanced selection. In one aspect, the method comprises crossing NUN 05048 SPS or its progeny, or a plant comprising all but 1, 2, or 3 or more of the morphological and physiological characteristics of NUN 05048 SPS (e.g., as listed in Table 1), with a different spinach plant, and wherein one or more offspring of the crossing are subject to one or more plant breeding techniques: recurrent selection, backcrossing, pedigree breeding, mass selection, mutation breeding and genetic marker enhanced selection (see e.g., Brotman et al., Theor Appl Genet (2002) 104:1055-1063). For breeding methods in general, see Principles of Plant Genetics and Breeding, 2007, George Acquaah, Blackwell Publishing, ISBN-13: 978-1-4051-3646-4.

In yet another aspect, the disclosure provides a method of producing a plant, comprising selfing a NUN 05048 SPS plant one or more times, and selecting a progeny plant from said selfing. In one aspect, the progeny plant retains all or all but one, two or three of the physiological and morphological characteristics of NUN 05048 SPS described above when, grown under the same environmental conditions. In another aspect, the progeny plant comprises all of the physiological and morphological characteristic of NUN 05048 SPS of Table 1.

In other aspects, the disclosure provides a progeny plant of NUN 05048 SPS such as a progeny plant obtained by further breeding of NUN 05048 SPS. Further breeding with NUN 05048 SPS includes selfing that variety and/or cross-pollinating NUN 05048 SPS with another spinach plant one or more times. In particular, the disclosure provides for a progeny plant that retains all the morphological and physiological characteristics of NUN 05048 SPS or, in another aspect, a progeny plant that retains all, or all but one, two or three, of the morphological and physiological characteristics of NUN 05048 SPS, optionally all or all but one, two or three of the characteristics as listed in Table 1, determined at the 5% significance level for numerical characteristics, when grown under the same environmental conditions. In another aspect, the progeny is a first generation progeny, i.e., the ovule or the pollen (or both) used in the crossing is an ovule or pollen of NUN 05048 SPS, where the pollen comes from an anther of NUN 05048 SPS and the ovule comes from an ovary of NUN 05048 SPS. In another aspect, the disclosure provides for a vegetative reproduction of NUN 05048 SPS and a plant having all, or all but 1, 2, or 3 of the physiological and morphological characteristics of NUN 05048 SPS (e.g., as listed in Table 1).

The disclosure also provides a method for collecting pollen of NUN 05048 SPS, comprising collecting pollen from a NUN 05048 SPS plant. Alternatively, the method comprises growing a NUN 05048 SPS plant until at least one flower contains pollen and collecting the pollen. In a particular aspect, the pollen is collected when it is mature or ripe. A suitable method for collecting pollen comprises collecting anthers or the part of the anther that contains pollen, for example, by cutting the anther or the part of the anther off. Pollen can be collected in a container. Optionally, collected pollen can be used to pollinate a spinach flower.

The morphological and/or physiological differences between two different individual plants described herein (e.g., between NUN 05048 SPS and a progeny of NUN 05048 SPS) or between a plant of NUN 05048 SPS or progeny of said variety, or a plant having all, or all but 1, 2, or 3, of the physiological and morphological characteristics of NUN 05048 SPS (or all, or all but 1, 2, or 3 of the characteristics as listed in Table 1) and another known variety can easily be established by growing said variety under the same environmental conditions (in the same field, optionally next to each other), preferably repeated in several locations which are suitable for cultivation of NUN 05048 SPS, and measuring the morphological and physiological characteristics of a representative number of plants (e.g., to calculate an average value and to determine the variation range/uniformity within the variety). For example, trials can be carried out in Acampo Calif., USA (N 38 degrees 07'261"/W 121 degrees 18'807", USA, whereby various characteristics, for example, maturity, days from seeding to harvest, plant habit, plant attitude, leaf shape, leaf color, disease resistance, insect resistance, can be measured and directly compared for species of spinach. Thus, the disclosure comprises spinach plant having one, two or three physiological and/or morphological characteristics which are different from those of the plant of NUN 05048 SPS, and which otherwise has all the physiological and morphological characteristics of the plant of NUN 05048 SPS, when determined at the 5% significance level for plants grown under the same environmental conditions. In another aspect, the different characteristic is affected by a mutation, optionally induced mutation, or by transformation.

The morphological and physiological characteristics of NUN 05048 SPS are provided in Table 1, as collected in a trial according to USDA and/or UPOV standards. The morphological and/or physiological characteristics may vary somewhat with variation in the environment (such as temperature, light intensity, day length, humidity, soil, fertilizer use, disease vectors), which is why a comparison under the same environmental conditions is preferred. Colors can best be measured using the Royal Horticultural Society (RHS) Chart.

The disclosure provides for methods of producing a plant comprising all but 1, 2, or 3 or more of the morphological and physiological characteristics of NUN 05048 SPS (e.g., as listed in Table 1), but which are still genetically closely related to said variety. The relatedness can, for example, be determined by fingerprinting techniques (e.g., making use of isozyme markers and/or molecular markers such as Single-nucleotide polymorphism (SNP) markers, amplified fragment length polymorphism (AFLP) markers, microsatellites, minisatellites, Random Amplified Polymorphic DNA (RAPD) markers, restriction fragment length polymorphism (RFLP) markers and others). A plant is "closely related" to NUN 05048 SPS if its DNA fingerprint is at least 80%, 90%, 95% or 98% identical to the fingerprint of NUN 05048 SPS. In a particular aspect, AFLP markers are used for DNA fingerprinting (Vos et al. 1995, Nucleic Acid Research 23: 4407-4414). A closely related plant may have a Jaccard's Similarity index of at least about 0.8, preferably at least about 0.9, 0.95, 0.98 or more (Parvathaneni et al., J. Crop Sci. Biotech. 2011 (Mar.) 14 (1): 39-43).

The disclosure also provides a plant obtained or selected by applying these methods on NUN 05048 SPS. Such a plant may be produced by traditional breeding techniques, or mutation or transformation or, in another aspect, a plant may simply be identified and selected amongst plants of said variety, or progeny of said variety, e.g., by identifying a variant of NUN 05048 SPS that differs from NUN 06202 SPS in one, two or three of the morphological and/or physiological characteristics (e.g., characteristics listed in Table 1). In one aspect, the disclosure provides a NUN 05048 SPS plant having a Jaccard's Similarity index with NUN 05048 SPS of at least 0.8, e.g., at least 0.85, 0.9, 0.95, 0.98 or even at least 0.99.

In some aspects, the disclosure provides a spinach plant comprising genomic DNA having at least 95%, 96%, 97%, 98% or 99% sequence identity compared to the genomic DNA sequence of a plant of NUN 05048 SPS as deposited under Accession Number NCIMB 42856. In some aspects, the spinach plant further comprises all or all but 1, 2, or 3 of the morphological and physiological characteristics of NUN 05048 SPS (e.g., as listed in Table 1). In other aspects, the spinach plant is a hybrid derived from a seed or plant of NUN 05048 SPS For the purpose of this disclosure, the "sequence identity" of nucleotide sequences, expressed as a percentage, refers to the number of positions in the two optimally aligned sequences which have identical residues (×100) divided by the number of positions compared. A gap, i.e., a position in the pairwise alignment where a residue is present in one sequence but not in the other, is regarded as a position with non-identical residues. A pairwise global sequence alignment of two nucleotide sequences is found by aligning the two sequences over the entire length according to the Needleman and Wunsch global alignment algorithm described in Needleman and Wunsch, 1970, J. Mol. Biol. 48(3):443-53). A full implementation of the Needleman-Wunsch global alignment algorithm is found in the needle program in The European Molecular Biology Open Software Suite (EMBOSS, Rice et al., Trends in Genetics June 2000, vol. 16, No. 6. pp.276-277).

The description also provides methods for determining the identity of parental lines of plants described herein, in particular the identity of the female line. WO2013/182646, which is hereby incorporated by reference, relates to a non-destructive method for analyzing maternal DNA of a seed. In this method, the DNA is dislodged from the seed coat surface and can be used to collect information on the genome of the maternal parent of the seed. This method for analyzing maternal DNA of a seed comprises contacting a seed with a fluid to dislodge DNA from the seed coat surface, and analyzing the DNA thus dislodged from the seed coat surface using methods known in the art. The skilled person is thus able to determine whether a seed has grown on a plant of NUN 05048 SPS or is a progeny of NUN 05048 SPS, because the seed coat of the seed is a maternal tissue genetically identical to NUN 05048 SPS. In one aspect, the disclosure relates to a maternal tissue of NUN 05048 SPS. In another aspect, the disclosure relates to a spinach seed comprising a maternal tissue of NUN 05048 SPS. In another particular aspect, the disclosure provides a method of identifying the female parental line of NUN 05048 SPS by analyzing the seed coat of a seed of that variety. In another aspect, the skilled person can determine whether a seed is grown on NUN 05048 SPS by analyzing the seed coat or another maternal tissue of said seed.

By crossing and/or selfing (one or more) single traits may be introduced into NUN 05048 SPS (e.g., using backcrossing breeding schemes), while retaining the remaining morphological and physiological characteristics of said variety and/or while retaining one or more or all distinguishing characteristics. A single trait converted plant may thereby be produced. For example, disease resistance genes may be introduced, genes responsible for one or more quality traits, yield, etc. Both single genes (e.g., dominant or recessive) and one or more QTLs (quantitative trait loci) may be transferred into NUN 05048 SPS by breeding with said variety.

Alternatively, a single trait converted plant or single locus converted plant of NUN 05048 SPS may be produced by (i) genetically transforming or mutating cells of NUN 05048 SPS; (ii) growing the cells into a plant; and (iii) optionally selecting a plant that contains the desired single locus conversion. Methods for genetically transforming or mutating a plant cell are known in the art.

Any pest or disease resistance genes may be introduced into NUN 05048 SPS, progeny of NUN 05048 SPS or into a plant comprising all but 1, 2, or 3 or more of the morphological and physiological characteristics of NUN 05048 SPS (e.g., as listed in Table 1). Resistance to one or more of the following diseases or pests is preferably introduced into plants described herein: *Peronospora farinosa* f.sp. *spinaciae*, e.g. to race 1-17 or new races and/or race UA510CC (Pf13) or other isolates; white rust (*Albugo occidentalis*), *Fusarium oxysporum* f.sp *spinaciae, Pythium* resistance, *Rhizoctonia* resistance, *Colletotrichum anthracnose* resistance, *Cercospora beticola* resistance, *Verticillium dahliae* resistance, *Phytophthora* ssp resistance, *Stemphylium* leaf spot resistance, Curly Top Virus resistance, Cucumber Mosaic Virus (CMV) resistance, Impatiens Necrotic Spot Virus (INSV), Beet Yellows and/or Beet mosaic resistance, leaf miner resistance. Other resistance genes, against pathogenic viruses, fungi, bacteria, nematodes, insects or other pests may also be introduced.

The disclosure also provides a NUN 05048 SPS plant, a sample of its seed to be deposited under Accession Number NCIMB 42856, comprising a single locus conversion. In another aspect, the single locus conversion confers a trait wherein the trait is yield, storage, color, flavor, male sterility, herbicide tolerance, insect resistance, pest resistance, disease resistance, environmental stress tolerance, modified carbohydrate metabolism, modified protein metabolism or ripening.

In one aspect, a plant of NUN 05048 SPS may also be mutated (by e.g., irradiation, chemical mutagenesis, heat treatment, etc.) and mutated seeds or plants may be selected in order to change one or more characteristics of said variety. Methods such as TILLING may be applied to populations in order to identify mutants. Similarly, NUN 05048 SPS may be transformed and regenerated, whereby one or more chimeric genes are introduced into the variety or into a plant comprising all but 1, 2, 3, or more of the morphological and physiological characteristics (e.g., as listed in Table 1). Transformation can be carried out using standard methods, such as *Agrobacterium tumefaciens* mediated transformation or biolistics, followed by selection of the transformed cells and regeneration into plants. A desired trait (e.g., gene(s) conferring pest or disease resistance, or tolerance for protection, etc.) can be introduced into NUN 05048 SPS, or progeny of said variety, by transforming said variety or progeny of said variety with a transgene that confers the desired trait, wherein the transformed plant retains all or all but one, two or three of the morphological and or physiological characteristics of NUN 05048 SPS and contains the desired trait. In another aspect, the transformation or mutation confers a trait wherein the trait is yield, color, herbicide tolerance, insect resistance, pest resistance, disease resistance, environmental stress tolerance, modified carbohydrate metabolism, modified protein metabolism or *Peronospora* resistance.

The disclosure also provides a plant or a plant cell comprising a desired trait produced by mutating at least one cell of NUN 05048 SPS and selecting a cell or a plant comprising the desired trait, wherein the mutated plant retains all or all but one, two or three of the morphological and physiological characteristics of NUN 05048 SPS, and contains the desired trait and wherein a representative sample of seed of NUN 05048 SPS has been deposited under Accession Number NCIMB 42856. In a further aspect, the desired trait is yield, color, herbicide tolerance, insect resistance, pest resistance, disease resistance, environmental stress tolerance, modified carbohydrate metabolism, modified protein metabolism or *Peronospora* resistance.

In one aspect, the disclosure provides a method for inducing mutation in NUN 05048 SPS comprising:
a. exposing a seed, a plant or a plant part or a cell of NUN 05048 SPS to a mutagenic compound or to radiation, wherein a representative sample of seed of NUN 05048 SPS is deposited under Accession Number NCIMB 42856;
b. selecting a seed, a plant or a plant part or a cell of NUN 05048 SPS having a mutation; and
c. optionally growing and/or multiplying the seed, plant or plant part or cell of NUN 05048 SPS having the mutation.

The disclosure also provides a plant having one, two or three physiological and/or morphological characteristics which are different from those of NUN 05048 SPS and which otherwise has all the physiological and morphological characteristics of said variety, wherein a representative sample of seed of variety NUN 05048 SPS has been deposited under Accession Number NCIMB 42856. In particular, variants are encompassed which differ from NUN 05048 SPS in, one, two or three of the characteristics mentioned in Table 1.

A part of NUN 05048 SPS (or of progeny of said variety or of a plant having all physiological and/or morphological characteristics but one, two or three which are different from those of said variety) encompasses any cells, tissues, organs obtainable from the seedlings or plants, such as but not limited to: a spinach leaf or a part thereof, a cutting, hypocotyl, cotyledon, seed coat, pollen and the like. Such parts can be stored and/or processed further. The disclosure further provides for food or feed products comprising a part of NUN 05048 SPS or a part of progeny of said variety, or a part of a plant having all but one, two or three physiological and/or morphological characteristics of NUN 05048 SPS, comprising one or more of such parts, optionally processed (such as canned, chopped, cooked, roasted, in a sauce, in a sandwich, pasted, puréed or concentrated, juiced, frozen, dried, pickled, or powdered).

The disclosure also provides a plant comprising at least a first set of the chromosomes of NUN 05048 SPS, a sample of seed to be deposited under Accession Number NCIMB 42856.

In one aspect, the disclosure provides a haploid plant and/or a doubled haploid plant of NUN 05048 SPS, or a plant having all but one, two or three physiological and/or morphological characteristics of NUN 05048 SPS, or progeny of any of these. Haploid and doubled haploid (DH) plants can, for example, be produced by cell or tissue culture and chromosome doubling agents and regeneration into a whole plant. For DH production, chromosome doubling may be induced using known methods, such as colchicine treatment or the like. In one aspect, the method comprises inducing a cell or tissue culture with a chromosome doubling agent, and regenerating the cells or tissues into a whole plant.

In yet another aspect, the disclosure provides for haploid plants and/or doubled haploid plants derived from NUN 05048 SPS that, when combined, make a set of parents of NUN 05048 SPS. The haploid plant and/or the doubled haploid plant of NUN 05048 SPS can be used in a method for generating parental lines of NUN 05048 SPS. In another aspect, the disclosure comprises a method for making doubled haploid cells from haploid cells of NUN 05048 SPS comprises doubling cells of NUN 05048 SPS with a doubling agent. There are various methods for doubling known in the art, including colchicine treatment.

Using methods known in the art such as "reverse synthesis of breeding lines" or "reverse breeding", it is possible to produce parental lines for a hybrid plant such as NUN 05048 SPS. Thus, a skilled person can take any individual heterozygous plant (called a "phenotypically superior plant" in Example 2 of WO2014/076249 hereby incorporated by reference in its entirety; NUN 05048 SPS is such a plant) and generate a combination of parental lines (reverse breeding parental lines) that, when crossed, produce the NUN 05048 SPS. It is not necessary that the reverse breeding parental lines are identical to the original parental lines. Such new breeding methods are based on the segregation of individual alleles in the spores produced by a desired plant and/or in the progeny derived from the self-pollination of that desired plant, and on the subsequent identification of suitable progeny plants in one generation, or in a limited number of inbred cycles. Such a method is known from WO2014/076249 or from Wijnker et al., Nature Protocols Volume: 9, Pages: 761-772 (2014) DOI: doi:10.1038/nprot.2014.049, which are hereby incorporated by reference in their entireties. Thus, the disclosure provides a method for producing parental lines for a hybrid organism (e.g., NUN 05048 SPS), comprising: a) defining a set of genetic markers present in a heterozygous form (H) in a partially heterozygous starting organism; b) producing doubled haploid lines from spores of the starting organism; c) genetically characterizing the doubled haploid lines thus obtained for the said set of genetic markers to determine whether they are present in a first homozygous form (A) or in a second homozygous form (B); and d) selecting at least one pair of doubled haploid lines that have complementary alleles for at least a subset of the genetic markers, wherein each member of the pair is suitable as a parental line for the hybrid organism. The disclosure also provides a method for producing parental lines for hybrid NUN 05048 SPS comprising: genetically characterizing a doubled haploid line from NUN 05048 SPS to determine whether one or more genetic markers are present in a first homozygous form or in a second homozygous form in said line, wherein the one or more genetic markers are present in a heterozygous form in NUN 05048 SPS; and selecting at least one pair of doubled haploid lines that have complementary alleles for the one or more the genetic markers, wherein each member of the pair is suitable as a parental line for a hybrid organism, optionally this method further comprises defining a set of genetic markers present in a heterozygous form in NUN 05048 SPS; and producing doubled haploid lines from NUN 05048 SPS. Doubled haploid lines generated as described herein can be used in such a method.

Thus, in one aspect, the disclosure relates to a method of producing a combination of parental lines of a plant of NUN 05048 SPS comprising making doubled haploid cells from haploid cells from said plant or a seed of that plant; and optionally crossing these parental lines to produce and collecting seeds. In another aspect, the disclosure relates to a combination of parental lines produced by this method. In still another aspect the combination of parental lines can be used to produce a seed or plant of NUN 05048 SPS when these parental lines are crossed. In still another aspect, the disclosure relates to a combination of parental lines from which a seed or plant having all physiological and/or morphological characteristics of NUN 05048 SPS (when the characteristics are determined at the 5% significance level for plants grown under the same conditions).

In another aspect, the disclosure provides a method of introducing a single locus conversion or single trait conversion or a desired trait into NUN 05048 SPS comprising:
a. obtaining a combination of a parental lines of NUN 05048 SPS, optionally through reverse synthesis of breeding lines,
b. introducing a single locus conversion or single trait conversion or a desired trait in at least one of the parents of step a to obtain a converted parent; and
c. crossing the converted parent with the other parent of step a to obtain seed of NUN 05048 SPS A combination of a male and a female parental line of NUN 05048 SPS can be generated by methods described herein, for example, through reverse synthesis of breeding lines.

In another aspect, the disclosure provides a method of introducing a single locus conversion or single trait conversion or a desired trait into NUN 05048 SPS, comprising introducing a single locus conversion or single trait conversion or a desired trait in at least one of the parents of NUN 05048 SPS to obtain a converted parent; and crossing the converted parent with the other parent of NUN 05048 SPS to obtain seed of NUN 05048 SPS.

In a further aspect, introducing a single locus conversion in at least one of the parent plants comprises:
i. obtaining a cell or tissue culture of cells of the parental line of NUN 05048 SPS;
ii. genetically transforming or mutating said cells;
iii. growing the cells into a plant; and
iv. optionally selecting plants that contain the single locus conversion, the single trait conversion or the desired trait.

In another method, the step of introducing a single locus conversion in at least one of the parents comprises genetically transforming or mutating cells the parental line of NUN 05048 SPS; growing the cells into a plant; and optionally selecting plants that contain the single locus conversion, the single trait conversion or the desired trait.

In another aspect, introducing a single locus conversion or a single trait conversion or a desired trait in at least one of the parent plants comprises:
i. crossing the parental line of NUN 05048 SPS with a second spinach plant comprising the single locus conversion, the single trait conversion or the desired trait;
ii. selecting F1 progeny plants that contain the single locus conversion, the single trait conversion or the desired trait;
iii. crossing said selected progeny plants of step ii with the parental line of step i, to produce a backcross progeny plant;
iv. selecting backcross progeny plants comprising the single locus conversion, the single trait conversion or the desired trait and otherwise all or all but one, two or three of the morphological and physiological characteristics the parental line of step i to produce selected backcross progeny plants; and
v. optionally repeating steps iii and iv one or more times in succession to produce selected second, third or fourth or higher backcross progeny plants comprising the single locus conversion, the single trait conversion or the desired trait and otherwise all or all but one, two or three of the morphological and physiological characteristics the parental line of step i to produce selected backcross progeny plants, when grown in the same environmental conditions.

The disclosure further relates to plants obtained by this method.

In any of the above methods where the single locus conversion concerns a trait, the trait may be yield or pest resistance or disease resistance. In one aspect, the trait is disease resistance and the resistance is conferred to *Peronospora farinose* f.sp. *spinaciae*, e.g., to race 1-17 or new races and/or race UA510C (Pfl3) or other isolates; white rust (*Albugo occidentalis*), *Fusarium oxysporum* f.sp *spinaciae*, *Pythium* resistance, *Rhizoctonia* resistance, *Colletotrichum anthracnose* resistance, *Cercospora beticola* resistance, *Verticillium dahliae* resistance, *Phytophthora* ssp resistance, *Stemphylium* leaf spot resistance, Curly Top Virus resistance, Cucumber Mosaic Virus (CMV) resistance, Impatiens Necrotic Spot Virus (INSV), Beet Yellows and/or Beet mosaic resistance, leaf miner resistance. Other resistance genes, against pathogenic viruses, fungi, bacteria, nematodes, insects or other pests may also be introduced.

The disclosure also provides a combination of parental lines which, when crossed, produce a seed or plant having all physiological and/or morphological characteristics of NUN 05048 SPS but one, two or three which are different (when grown under the same environmental conditions), as well as a seed or plant having all physiological and/or morphological characteristics of NUN 05048 SPS but one, two or three which are different (when the characteristics are determined at the 5% significance level for plants grown under the same conditions).

In another aspect, the disclosure provides a method of determining the genotype of a plant described herein comprising detecting in the genome (e.g., a sample of nucleic acids) of the plant at least a first polymorphism or an allele. The skilled person is familiar with many suitable methods of genotyping, detecting a polymorphism or detecting an allele including restriction fragment length polymorphism identification (RFLP) of genomic DNA, random amplified polymorphic detection (RAPD) of genomic DNA, amplified fragment length polymorphism detection (AFLP), polymerase chain reaction (PCR), DNA sequencing, allele specific oligonucleotide (ASO) probes, and hybridization to DNA microarrays or beads. Alternatively, the entire genome could be sequenced. The method may, in certain aspects, comprise detecting a plurality of polymorphisms in the genome of the plant, for example, by obtaining a sample of nucleic acid from a plant and detecting in said nucleic acids a plurality of polymorphisms. The method may further comprise storing the results of the step of detecting the plurality of polymorphisms on a computer readable medium All documents (e.g., patent publications) are herein incorporated by reference in their entirety, including the following cited references:

"Guidelines for the Conduct of Tests for Distinctness, Uniformity and Stability, TG/55/7 (Geneva, 2007), upov.int/en/publications/tg-rom/tg055/tg_55_7.pdf
"OBJECTIVE DESCRIPTION OF VARIETY—Spinach (*Spinacia oleracea* L.)" ams.usda.gov/ under sites/default/files/media/3-Spinach%20ST-470-83%202015.pdf
Acquaah Principles of Plant Genetics and Breeding, 2007, Blackwell Publishing, ISBN-13: 978-1-4051-3646-4.
Brotman et al., Theor Appl Genet (2002) 104:1055-1063).
Colijn-Hooymans (1994), Plant Cell, Tissue and Organ Culture 39: 211-217)
Needleman and Wunsch, 1970, J. Mol. Biol. 48(3):443-53
Parvathaneni et al., J. Crop Sci. Biotech. 2011 (Mar.) 14 (1): 39-43
Ren et al., In Vitro Cell. Dev. Biol.—Plant (2013) 49:223-229
Rice et al., Trends in Genetics June 2000, vol. 16, No. 6. pp.276-277
Vos et al. 1995, Nucleic Acid Research 23: 4407-4414
Wijnker et al., Nature Protocols Volume: 9, Pages: 761-772 (2014) DOI: 10.1038/nprot.2014.049
WO2013182646
WO2014076249

EXAMPLES

Development of NUN 05048 SPS

The hybrid NUN 05048 SPS was developed from a male and female proprietary inbred line of Nunhems. The female and male parents were crossed to produce hybrid (F1) seeds of NUN 05048 SPS. The seeds of NUN 05048 SPS can be grown to produce hybrid plants and parts thereof (e.g., spinach leaves). The hybrid NUN 05048 SPS can be propagated by seeds or vegetatively.

The hybrid variety is uniform and genetically stable. This has been established through evaluation of horticultural characteristics. Several hybrid seed production events resulted in no observable deviation in genetic stability. Coupled with the confirmation of genetic stability of the female and male parents the Applicant has concluded that NUN 05048 SPS is uniform and stable.

Deposit Information

A total of 2500 seeds of the hybrid variety NUN 05048 SPS is deposited according to the Budapest Treaty by Nunhems B.V. on Oct. 30, 2017, at the NCIMB Ltd., Ferguson Building, Craibstone Estate, Bucksburn, Aberdeen AB21 9YA, United Kingdom (NCIMB). The deposit will be assigned NCIMB number 42856. A deposit of NUN 05048 SPS and of the male and female parent line is also maintained at Nunhems B.V.

Access to the deposits will be available during the pendency of this application to persons determined by the Director of the U.S. Patent Office to be entitled thereto upon request. Subject to 37 C.F.R. § 1.808(b), all restrictions imposed by the depositor on the availability to the public of the deposited material will be irrevocably removed upon the granting of the patent. The deposit will be maintained for a period of 30 years, or 5 years after the most recent request, or for the enforceable life of the patent whichever is longer, and will be replaced if it ever becomes nonviable during that period. Applicant does not waive any rights granted under this patent on this application or under the Plant Variety Protection Act (7 U.S.C. § 2321 et seq.).

Table 1 shows a comparison between NUN 05048 SPS and its Reference variety based on several trials in various locations. In Table 1, the UPOV characteristics of NUN 05048 SPS and its Reference variety are listed. The most similar variety to NUN 05048 SPS is referred to as Reference variety, a variety from Nunhems with the commercial name Antalia. Table 2 shows a comparison between NUN 05048 SPS and Antalia based on a separate trial

TABLE 1

Characteristics of NUN 05048 SPS and Reference Variety Antalia

| Characteristic | Antalia | NUN 05048 SPS |
|---|---|---|
| Seedling: length of cotyledon (3 short/5 medium/7 long) | 5 | 5 |
| Leaf: anthocyanin coloration of petioles and veins (1 absent/9 present) | 1 | 1 |
| Leaf blade: intensity of green color (1 very light/2 very light to light/3 light/4 light to medium/5 medium/6 medium to dark/7 dark/8 dark to very dark/9 very dark) | 6 | 8 |
| Leaf blade: blistering (1 absent or very weak/2 very weak to weak/3 weak/4 weak to medium/5 medium/6 medium to strong/7 strong/8 strong to very strong/9 very strong) | 4 | 2 |
| Leaf blade: lobing: 1 = absent or very weak; 3 = weak; 5 = medium; 7 = strong | 5 | 1 |
| Petiole: attitude (1 erect/3 semi erect/5 horizontal) | 3 | 1 |
| Petiole: length (1 very short/3 short/5 medium/7 long/9 very long) | 2 | 3 |
| Leaf blade: attitude (1 erect/3 semi erect/5 horizontal/7 semi-pendulous) | 5 | 1 |
| Leaf blade: shape (excluding basal lobes) (1 triangular/2 medium ovate/3 broad ovate/4 medium elliptic/5 broad elliptic/6 circular) | 6 | 1 |
| Leaf blade: curving of margin (1 incurved/2 flat/3 recurved) | 2 | 2 |
| Leaf blade: shape of apex (1 acute/2 obtuse/3 rounded) | 2 | 2 |
| Leaf blade: shape in longitudinal section (1 concave/2 flat/3 convex) | 2 | 2 |
| Seed: spines (harvest seed) (1 absent/9 present) | 1 | 1 |

TABLE 2

Objective Description of Spinach Variety NUN 05048 SPS and the Reference Variety based on a USDA trial

| Characteristics | Antalia | NUN 05048 SPS |
|---|---|---|
| Ploidy 1 = diploid; 2 = tetraploid; 3 = other | Diploid | Diploid |
| Maturity: | | |
| Growth rate: 1 = slow; 2 = medium (Long Standing Bloomsdale); 3 = fast (Dixie Market) | Medium | Slow |

TABLE 2-continued

Objective Description of Spinach Variety NUN 05048 SPS and the Reference Variety based on a USDA trial

| Characteristics | Antalia | NUN 05048 SPS |
|---|---|---|
| Days from planting to prime market stage | 30 | 33 |
| Plant (prime market stage): | | |
| Habit: 1 = flat (Viroflay); 2 = semi-erect (Long Standing Bloomsdale); 3 = erect (Virginia Savoy) | Semi-erect | Semi-erect |
| Size: 1 = small (America); 2 = medium; 3 = large (Giant Nobel) | Medium | Small to medium |
| Spread (cm): | 30.84 | 38.11 |
| Height (cm): | 10.56 | 10.07 |
| Seeding colyledon: | | |
| Width (mm): | 5.55 | 4.97 |
| Length (mm): | 38.5 | 63.3 |
| Tip: 1 = pointed; 2 = rounded | Rounded | Rounded |
| Color: 1 = light green; 2 = medium green; 3 = dark green; 4 = other | Medium green (RHS 146C) | Medium green (RHS 146B) |
| Leaf (first foliage leaves): | | |
| Base: 1 = V-shape; 2 = straight; 3 = lobed | V-shape | V-shape |
| Tip: 1 = round; 2 = round-pointed; 3 = pointed | Round | Round-pointed |
| Upper surface color: 1 = light green (Hollandia); 2 = medium green (Giant Nobel); 3 = dark green (Long Standing Bloomsdale) | Medium green (RHS I 46A) | Medium green (RIHS 137B) |
| Lower surface color (compared with upper surface): 1 = lighter; 2 = same; 3 = darker | Lighter (RHS 146B) | Lighter (RHS 137C) |
| 1$^{st}$ Leaf length (mm): | 28.25 | 37.40 |
| 1$^{st}$ Leaf width (mm): | 17.57 | 70.69 |
| 1$^{st}$ Leaf petiole length (pm): | 22.9 | 20.35 |
| Leaf (prime market stage): | | |
| Surface: 1 = smooth (Viroflay); 2 = semi-savory (Northland); 3 = Savoy (Virginia Savoy) | Semi-savoy | Semi-savoy |
| Base: 1 = V-shaped; 2 = straight; 3 = lobed | Lobed | Lobed |
| Tip; 1 = round; 2 = round-pointed; 3 = pointed | Round-pointed | Round-pointed |
| Upper surface color chart | RHS N137A | RHS139A |
| Lower surface color (compared with upper surface): 1 = lighter; 2 = same; 3 = darker | Lighter (RHS 146B) | Lighter (RHS 137B) |
| Luster: 1 = glossy; 2 = dull | Glossy | Glossy |
| Blade size: 1 = small (Long Standing Bloomsdale); 2 = medium (Virginia Savoy); 3 large (Giant Nobel) | Medium | Medium |
| Petiole color: 1 = white; 2 = light yellow; 3 = light green; 4 = medium green | Light green (RHS 137C) | Light green (RHS 144A) |
| Petiole red pigmentation: 1 = present; 2 = absent | Absent | Absent |
| Petiole length to the blade (cm): | 5.15 | 4.51 |
| Petiole diameter (mm): | 10.29 | 9.27 |
| Petiole diameter: 1 = small; 2 = medium; 3 large (Giant Nobel) | Medium | Medium |
| Leaf length (cm) | 15.03 | 18.68 |
| Leaf width (mm): | 107.63 | 113.97 |

Tables 1 and 2 contain typical values. Values may vary due to environment. Other values that are substantially equivalent are also within the scope of the disclosure. N.A.=not applicable; n.r.=not recorded.

What is claimed is:

1. A plant, plant part or seed of spinach variety NUN 05048 SPS, wherein representative sample of seed of said spinach variety is deposited under Accession Number NCIMB 42856.

2. The plant part of claim 1, wherein said plant pan is a leaf, pollen, an ovule, a fruit, a scion, a root, a rootstock, a cutting, a flower, or a cell.

3. A seed that produces the plant of claim 1.

4. A seed grown on the plant of claim 1.

5. A spinach plant or a part thereof having all of the physiological and morphological characteristics of the plant of claim 1.

6. A spinach plant or part thereof which does not differ from the plant of the plant of variety NUN 05048 SPS as determined at the 5% significance level when grown under the same environmental conditions, and wherein a representative sample of seed of said spinach variety has been deposited under Accession Number NCIMB 42856.

7. A tissue or cell culture comprising regenerable cells of the plant or plant part of claim 1.

8. The tissue or cell culture according to claim 7, comprising cells or protoplasts derived from a plant part, wherein the plant part is, a meristem, a cotyledon, a hypocotyl, pollen, a leaf, an anther, a root, a root tip, a pistil, a petiole, a flower, a fruit, a stem, or a stalk.

9. A spinach plant regenerated from the tissue or cell culture of claim 7, wherein the plant has all of the physiological and morphological characteristics of the plant of variety NUN 05048 SPS, when the characteristics are determined at the 5% significance level for plants grown under the same environmental conditions, and wherein a representative sample of seed of spinach variety NUN 05048 SPS is deposited under Accession Number NCIMB 42856.

10. A method of producing the plant of claim 1, comprising vegetatively propagating at least a part of a plant of variety NUN 05048 SPS, wherein a representative sample of seed of said spinach variety is deposited under Accession Number NCIMB 42856.

11. The method of claim 10, wherein the vegetative propagation comprises regenerating a whole plant from said part of a plant of variety NUN 05048 SPS, wherein a representative sample of seed of said variety is deposited under Accession Number NCIMB 42856.

12. The method of claim 10, wherein said part is a cutting, a culture or a tissue culture.

13. A vegetative propagated plant of claim 1, or a part thereof, wherein the vegetative propagated plant has all of the physiological and morphological characteristics of the plant of variety NUN 05048 SPS, when the characteristics are determined at the 5% significance level for plants grown under the same environmental conditions, and wherein a representative sample of seed of spinach variety NUN 05048 SPS is deposited under Accession Number NCIMB 42856.

14. A method of producing a spinach plant, comprising crossing the plant of claim 1 with a second spinach plant at least once, and selecting a progeny spinach plant from said crossing, and optionally allowing the progeny spinach plant to form seed.

15. A spinach plant having one physiological or morphological characteristic which is different from the plant of claim 1, and which otherwise has all the physiological and morphological characteristics of the plant of variety NUN 05048 SPS, when determined at the 5% significance level for plants grown under the same environmental conditions.

16. A plant of spinach variety NUN 05048 SPS further comprising a single locus conversion, wherein single locus conversion is introduced by genetic transformation, wherein said plant otherwise has all of the morphological and physiological characteristics of the plant of claim 1, wherein a representative sample of seed of spinach variety is deposited under Accession Number NCIMB 42856, when said characteristics are determined at 5% significance level for plants grown under the same environmental conditions, and wherein the single locus conversion confers male sterility, herbicide tolerance, insect resistance, pest resistance, disease resistance, environmental stress tolerance, modified carbohydrate metabolism, or modified protein metabolism.

17. A method of producing double haploids of the plant of variety NUN 0548 SPS comprising making doubled haploid cells from haploid cells from the plant or seed of NUN 05048 SPS, wherein a representative sample of seed of spinach variety NUN 05048 SPS is deposited under NCIMB 42856.

18. A container comprising the plant, plant part or seed of claim 1.

19. A food, a feed product or a processed product comprising the plant part of claim 2, wherein the plant part is a spinach leaf, or a part thereof.

20. A method of producing a spinach leaf, comprising growing the plant of claim 1 until it develops at least one leaf, and collecting the leaf.

21. A method for collecting pollen of variety NUN 05048 SPS, comprising growing the plant of claim 1 until at least one flower contains pollen, and collecting the pollen.

22. A method of producing a spinach plant having a trait, comprising mutating a plant or plant part of spinach variety NUN 05048 SPS and selecting a mutated plant with a desired trait, wherein the mutated plant contains the desired trait and otherwise retains all the physiological and morphological characteristics of variety NUN 05048 SPS, when the characteristics are determined at the 5% significance level for plants grown under the same environmental conditions, and wherein a representative sample of seed of said spinach variety is deposited under Accession Number NCIMB 42856.

23. The method of claim 22, wherein the desired trait is male sterility, herbicide tolerance, insect resistance, pest resistance, disease resistance, environmental stress tolerance, *Peronospora* resistance, modified carbohydrate metabolism, or modified protein metabolism.

\* \* \* \* \*

UNITED STATES PATENT AND TRADEMARK OFFICE
CERTIFICATE OF CORRECTION

| | |
|---|---|
| PATENT NO. | : 10,383,300 B2 |
| APPLICATION NO. | : 16/032942 |
| DATED | : August 20, 2019 |
| INVENTOR(S) | : Frederike Koerber |

Page 1 of 1

It is certified that error appears in the above-identified patent and that said Letters Patent is hereby corrected as shown below:

In the Claims

Column 22, Line 1, Claim 2 replace "pan" with -- part --

Signed and Sealed this
First Day of October, 2019

Andrei Iancu
*Director of the United States Patent and Trademark Office*